(12) United States Patent
Jin

(10) Patent No.: US 7,713,555 B2
(45) Date of Patent: May 11, 2010

(54) LUBRICANT ADDITIVE TO ENHANCE STAYING POWER OF MALE ERECTILE FUNCTION

(76) Inventor: Cheng Jin, 376 S. Lemon Creek Dr., # A, Walnut, CA (US) 91789

( * ) Notice: Subject to any disclaimer, the term of this patent is extended or adjusted under 35 U.S.C. 154(b) by 117 days.

(21) Appl. No.: 11/780,004

(22) Filed: Jul. 19, 2007

(65) Prior Publication Data

US 2009/0022829 A1    Jan. 22, 2009

(51) Int. Cl.
*A01N 65/00*    (2006.01)
(52) U.S. Cl. .................................................. 424/725
(58) Field of Classification Search ................ None
See application file for complete search history.

(56) References Cited

FOREIGN PATENT DOCUMENTS

WO    WO 9925368    *    5/1999

* cited by examiner

Primary Examiner—Michael V Meller
(74) Attorney, Agent, or Firm—Jen-Feng Lee

(57) ABSTRACT

Present invention provides an efficient way of enhancing male erectile function, without the fear of unknown long-term ill-effect as a result of taking medication orally. The additive of present invention can be used by condom manufacturers directly as part of the lubricant coating. The composition of the additive pursuant to present invention will cause the dilating and expansion of arteries sending blood to the chambers of corpora cavernosa and corpus spongiosum, and at the same time, cause the restricting and contracting of veins that take blood away. As a result, the hardness of penile erection is increases. Particularly, the staying power is enhanced and time of erection is prolonged, leading to increased sexual intercourse time and better sexual satisfaction.

1 Claim, No Drawings

LUBRICANT ADDITIVE TO ENHANCE STAYING POWER OF MALE ERECTILE FUNCTION

FIELD AND BACKGROUND OF THE INVENTION

The present invention relates to an additive that can be added to the lubricant used on, or applied directly to the inside of, a condom that will have the effect of enhancing male erectile function.

OBJECTS AND SUMMARY OF THE INVENTION

Present invention provides an efficient way of enhancing male erectile function, without the fear of unknown long-term ill-effect as a result of taking medication orally. The additive of present invention can be used by condom manufacturers directly as part of the lubricant coating. For consumers interested in enhancing their sexual performance, they can apply present additive to condom, or purchase condoms that include products made pursuant to the disclosure of present invention.

The ingredients used in present invention, after clinical trials, have shown to increase the hardness of penile erection and particularly to enhance the staying power of penile erection for sexual intercourse, leading to better sexual satisfaction.

DETAILED DESCRIPTION OF THE PREFERRED EMBODIMENT

Male erectile function is achieved by filling blood into the two corpora cavernosa chambers (upper side) and the corpus spongiosum chamber (under side). There is no erectile bone supporting the state of penile engorgement. The status of erection completely depends on the retention of blood in these sponge-like chamber tissues mentioned above.

While there are available medications to enhance and sustain the status of erection, concerns still linger about unknown long-term ill-effect, as happened all the time in all kinds of drugs even approved by FDA.

Present invention avoids such oral administering of erectile enhancement route, but by using additive that applied externally to the skin tissue of penile glans and the foreskin, alleviating the concern of long-term undiscovered side effect like many drugs taken orally.

The composition of the additive pursuant to present invention will cause the dilating and expansion of arteries sending blood to corpora cavernosa and corpus spongiosum, and at the same time, cause the restricting and contracting of veins that take blood away.

As a result, users can achieve a fuller engorgement (erection).

Moreover, some of the ingredients in present disclosure work to slow the transmission of nervous impulse by nerve cells and nerve endings located at and near penile glans. At the time, the sensation associated with sexual pleasure, leading up to the point of orgasm, is not affected.

Male users of present invention will likely be able to sustain longer period of penile erection, with increased harness, before penis returns to its flaccid state due to the blood in the three chambers being taken back to other body parts where the blood came from.

The ingredients for additive of present invention are based upon 500 g of silicon cream commonly used by condom manufacturers as the base lubricant coated to the inside of condoms. This is known prior art and require no disclosure and is not claimed as part of present invention except to the extent it is combined in other disclosure.

The ingredients included:
a. 0.5-5 g Dyclonine with concentration between 0.1-1%;
b. 5-10 g Nitroglycerin with concentration between 1-2%;
c. 20 g Yohimbine;
d. 1 g Herba Asari with concentration at 0.2%;
e. 1 g Radix Stephaniae Tetrandrae with concentration at 0.2%;
f. 1 g Rhizoma Corydalis with concentration at 0.2%;
g. 5 g Azone with concentration at 1%;
h. 10-20 mg Prostaglandin E1; and,
i. 0.5-5 g Phentolamine with concentration at 0.1-1%.

Then, mix the above-stated ingredients into an asepsis container of 500 g silicon cream, using electro-motion blender to work on the compound for 15-20 minutes, pursuant to normal heating, distillation and dregs-removing process.

After the proper Ph balance is checked and the bacterium level check is satisfactory, as in the case of commonly adopted practice for producing the lubricant, the additive is ready for use, either coated directly to condoms, or added into the lubricant for coating into condoms.

The steps of mixing and then checking for Ph balance and bacterium safety will be treated as an element "j" when organized in claims.

Additionally, the following ingredients can be added to form a second formula, based upon the same 500 g cream:
k. 0.5-1.5 g Amethocaine with concentration at 0.1-0.3%;
l. 5-10 g Venerum Buforis with concentration at 1-2%;
m. 1 g Radix Aconiti; and,
n. 1 g Semen Strychni;

Additionally, the following ingredients can be added to the second formula, forming third ingredient formula, based upon the same 500 g cream:
o. 1 g Flos Daturae with concentration at 0.2%; and,
p. 25-50 g Papaverine with concentration at 5-10%.

The final mixture in second and third formula likewise need to pass the Ph balance and bacterium level check, as commonly administered in the industry, before it is ready for use to become part of the lubricant.

Note that in the second and third formula, the ingredients of Radix Aconiti, Semen Strychni and Flos Daturae refer to their cured and prepared form, so as to reduce the natural toxicity of these ingredients.

What is claimed is:

1. A lubricant additive to enhance the staying power for male erectile function, comprising the following ingredients:
a. 0.5-5 g Dyclonine at a concentration between 0.1-1%;
b. 5-10 g Nitroglycerin at a concentration between 1-2%;
c. 20 g Yohimbine;
d. 1 g Herba Asari at a concentration at 0.2%;
e. 1 g Radix Stephaniae Tetrandrae at a concentration at 0.2%;
f. 1 g Rhizoma Corydalis at a concentration at 0.2%;
g. 5 g Azone at a concentration at 1%;
h. 10-20 mg Prostaglandin E1; and
i. 0.5-5 g Phentolamine at a concentration at 0.1-1%; and wherein,
the ingredients are mixed into an asepsis container of 500 g silicon cream using an electro-motion blender for 15-20 minutes to yield the lubricant additive.

* * * * *